United States Patent

Kingsley et al.

Patent Number: 5,853,382
Date of Patent: Dec. 29, 1998

[54] BLOOD COLLECTION AND SEPARATION PROCESS

[75] Inventors: Gordon F. Kingsley; Thomas D. Headley, both of Wellesley; Lise N. Halpern, Wayland, all of Mass.

[73] Assignee: Transfusion Technologies Corporation, Natick, Mass.

[21] Appl. No.: 662,613

[22] Filed: Jun. 13, 1996

Related U.S. Application Data

[62] Division of Ser. No. 482,617, Jun. 7, 1995, Pat. No. 5,651,766.

[51] Int. Cl.⁶ .................................................. A61M 35/00
[52] U.S. Cl. .................................. 604/4; 210/782; 494/37
[58] Field of Search ....................... 604/4, 5, 6; 210/781, 210/782; 494/37

[56] References Cited

U.S. PATENT DOCUMENTS

| | | | |
|---|---|---|---|
| 3,373,096 | 3/1968 | Jones et al. | |
| 3,737,096 | 6/1973 | Jones et al. | 233/19 A |
| 4,007,871 | 2/1977 | Jones et al. | 233/27 |
| 4,010,894 | 3/1977 | Kellogg et al. | 233/27 |
| 4,056,224 | 11/1977 | Lolachi | 233/14 |
| 4,086,924 | 5/1978 | Latham, Jr. | 128/214 |
| 4,151,844 | 5/1979 | Cullis et al. | 128/214 |
| 4,285,464 | 8/1981 | Latham, Jr. | 233/26 |
| 4,303,193 | 12/1981 | Latham, Jr. | 233/23 A |
| 4,387,848 | 6/1983 | Kellogg et al. | 494/81 |
| 4,482,342 | 11/1984 | Lueptow et al. | 494/21 |
| 4,530,691 | 7/1985 | Brown | 494/45 |
| 4,643,714 | 2/1987 | Brose | 604/4 |
| 4,647,279 | 3/1987 | Mulzet et al. | 494/45 |
| 4,734,089 | 3/1988 | Cullis | 494/27 |
| 4,850,995 | 7/1989 | Tie et el. | 604/6 |
| 4,889,524 | 12/1989 | Fell et al. | 494/12 |
| 4,911,833 | 3/1990 | Schoendorfer et al. | 210/67 |

(List continued on next page.)

FOREIGN PATENT DOCUMENTS

| | | | |
|---|---|---|---|
| 2 047 110 A | 11/1980 | United Kingdom | A61M 1/03 |
| 96/11747 | 4/1996 | WIPO | B04B 5/04 |

OTHER PUBLICATIONS

U.S. Application No. 08/322,601, Headley et al., filed Oct. 13, 1994.

Primary Examiner—John G. Weiss
Assistant Examiner—Ki Yong O
Attorney, Agent, or Firm—Bronberg & Sunstein LLP

[57] ABSTRACT

A system compact enough to be located entirely beside the donor's chair, and able to process the blood while the donor is still resting in the chair after having donated the blood. The separated blood components (plasma and red blood cells) may be stored in their individual optimum environments immediately after the whole blood is drawn, and the blood does not need to be transported back to a separation laboratory for processing. The system includes a needle (72) (or other cannula-like device) for insertion into a vein of the donor and drawing whole blood therethrough, a rotor (2a) for holding the blood after it is drawn, and a motor (50) for spinning the rotor so as to cause the blood to separate into components, for example, plasma and red blood cells. The system also provides for a container for collecting a separated component. In a preferred embodiment two containers are used: the first container (92) for containing an anticoagulant, which is preferably added to the whole blood as it is drawn from the donor, and then for storing the plasma after it has been separated from the red blood cells, and the second container (91) for storing the separated red blood cells. The system further includes tubing (73), which may have valving (81) built into it and which may be acted on externally, so as to direct the blood components in the desired manner. The tubing connects the needle (72), the rotor (2a), and the first and second containers (92, 91). With the valving, the tubing is able to permit (i) the flow of whole blood from the needle (72) to the rotor (2a), (ii) the flow of anticoagulant from the first container (92) to the whole blood flowing from the needle to the rotor, (iii) the flow of plasma from the rotor to the first container, and (iv) the flow of red blood cells from the rotor to the second container (91).

16 Claims, 5 Drawing Sheets

U.S. PATENT DOCUMENTS

| | | | |
|---|---|---|---|
| 4,985,153 | 1/1991 | Kuroda et al. | 210/782 |
| 5,114,396 | 5/1992 | Unger et al. | 494/37 |
| 5,141,486 | 8/1992 | Antwiler | 494/37 |
| 5,234,403 | 8/1993 | Yoda et al. | 604/4 |
| 5,273,517 | 12/1993 | Barone et al. | 12/93 |
| 5,298,016 | 3/1994 | Gordon | 609/4 |
| 5,316,540 | 5/1994 | McMannis et al. | 494/37 |
| 5,318,512 | 6/1994 | Neuman | 604/6 |
| 5,368,542 | 11/1994 | McMannis et al. | 494/45 |
| 5,386,734 | 2/1995 | Pusinelli | 73/863.21 |
| 5,387,187 | 2/1995 | Fell et al. | 604/6 |
| 5,437,598 | 8/1995 | Antwiler | 494/1 |
| 5,470,483 | 11/1995 | Bene et al. | 210/741 |
| 5,484,396 | 1/1996 | Naficy | 604/4 |
| 5,514,716 | 5/1996 | Bauman et al. | 210/782 |

BLOOD COLLECTION AND SEPARATION PROCESS

This application is a divisional of U.S. application Ser. No. 08/482,617, filed Jun. 7, 1995 now U.S. Pat. No. 5,651,766, for an invention by Kingsley et al., which application is incorporated herein by reference.

TECHNICAL FIELD

This invention relates to a method of whole-blood collection and the preparation of components therefrom following collection.

BACKGROUND ART

In the conventional method of whole blood collection, a needle is placed in a vein in the donor's arm and whole blood flows by gravity into a bag which holds a quantity of anticoagulant solution, which prevents the blood from clotting. When a unit of whole blood, defined in the United States as 450 milliliters (ml), has been collected, the needle is removed from the vein and the blood bag is set aside for later transfer to the processing laboratory of the blood center.

It should be noted that the ratio of anticoagulant to whole blood is approximately one to seven; thus the amount of anticoagulant in the bag is 63 ml. It should also be noted that, while the ratio of anticoagulant to whole blood is one to seven after a full unit has been collected, the ratio of anticoagulant to whole blood is considerably higher than one to seven at the beginning of the collection. The red cells flowing into the collection bag at the beginning of the collection are, therefore, subject to "anticoagulant shock", which has the effect of damaging some of the red cells. As the collection proceeds, the ratio decreases.

In the processing laboratory, a technician places the bags of whole blood into a large, swinging bucket centrifuge, which must be carefully balanced as the bags are loaded. The centrifuge is started and the bags are spun at a high rate of speed. In the first of the bag while the platelet-rich plasma, which is lighter, rises to the top. When the bags are removed from the centrifuge, they must be handled carefully so as to avoid remixing.

The technician next places each bag in an "expresser" consisting of two rigid plates that are joined by a spring loaded hinge. One of the plates is fixed and the other is moveable. The blood bag is positioned between the two plates and the spring catch released causing the moveable plate to press against the bag. A port on the top of the bag is then opened and the platelet-rich plasma is expressed into an attached, empty bag. When the technician observes that red cells are about to reach the outlet port, the expression is stopped and the tubing clamped.

If platelets are to be separated, the bags containing the platelet rich plasma are returned to the centrifuge, the load is again balanced and a second spin begins, this time at a higher speed. This spin forces the platelets to the bottom of the bag and allows the lighter plasma to rise to the top. The expression process described above is then repeated so that the platelets can be diverted to a separate bag for storage. There are other variations of these blood-component collection and separation processes, including a process for collecting a buffy coat from the blood; all of the variations use centrifugation techniques similar to those described above. Although various devices have been developed and marketed whose function is to minimize the amount of labor required in the expression of components from one bag to another, these devices do not eliminate the centrifugation step described above. Furthermore, these devices are designed to be used in the component-preparation laboratory of the blood center and not at the point of whole blood collection.

It will be appreciated, therefore, that the conventional method of centrifuging and separating components from whole blood is a labor-intensive, manual process. In addition, in order to be convenient to volunteer donors, the majority of whole blood collections take place, not in the blood center, but in mobile units that travel to other locations, such as community centers, offices and factories. Because the bags of whole blood must then be transported back to the blood center for processing and because of the need to schedule the time of laboratory personnel, many hours can elapse between the completion of the collection and the time that component separation begins.

It should be noted that, if the plasma separated from the whole blood is to be used for the production of Factor VIII for transfusion to hemophiliacs, regulations require that the plasma separation must be completed and the plasma frozen within six hours of the time of the whole-blood collection. It can be demonstrated that, the sooner the plasma is frozen, the higher will be the recovery of Factor VIII. It should be further noted that, if the plasma is to be used for transfusion as Fresh Frozen Plasma, regulations require that the separated plasma be placed at −18° C. or lower within eight hours of collection from the donor. The practical consequence of these regulations is that blood banks must schedule the times of donations with the times at which laboratory personnel are available to prepare the components.

In addition to the conventional method of whole blood collection and component separation just described, individual blood components can be collected by a process called apheresis. In this process, the donor is connected to a cell separator, a needle is inserted in the donor's arm, an anticoagulant is added to the whole blood as it is drawn from the donor, and the anticoagulated whole blood is pumped into the rotor of the cell separator where centrifugal force causes the components to separate. The component that is to be retained is directed to a collection bag and the unwanted components are returned to the donor. This process of drawing and returning continues until the quantity of the desired component has been collected, at which point the process is stopped. Apheresis systems are used widely for the collection of single-donor platelets and single-donor plasma. A central feature of these apheresis devices, however, is that, while they separate blood components at the point of collection, they require that the unwanted components must be returned to the donor. This, in turn, means that apheresis devices must incorporate a variety of safety features, such as air detectors and pressure monitors, to protect the donor from harm while the donor is connected to the cell separator. Such safety mechanisms add cost and complexity to apheresis system equipment and disposables.

In contrast to apheresis systems, conventional whole blood collection systems do not return anything to the donor but, on the other hand, neither are they able to separate blood components at the site of collection. There is a need, therefore, for an improved method of whole blood collection and the preparation of components therefrom, without the complexity and expense of conventional apheresis devices, and without the labor-intensive, manual separation process described above.

SUMMARY OF THE INVENTION

The present invention provides a system for collecting and processing blood from a donor, wherein the system may be compact enough to be located entirely beside the donor's chair, and be able to process the blood while the donor is still resting in the chair after having donated the blood. Thus, the separated blood components (plasma and red blood cells) may be stored in their individual optimum environments immediately after the whole blood is drawn, and the blood does not need to be transported back to a separation laboratory for processing.

The system includes a needle (or other cannula-like device) for insertion into a vein of the donor and drawing whole blood therethrough, a variable-volume rotor for holding the blood after it is drawn, and means for spinning the rotor so as to cause the blood to separate into components, for example, plasma and red blood cells. The system also provides for a container for collecting a separated component. In a preferred embodiment two containers are used: the first container for containing an anticoagulant, which is preferably added to the whole blood as it is drawn from the donor, and then for storing the plasma after it has been separated from the red blood cells, and the second container for storing the separated red blood cells. The system further includes tubing, which may have valving built into it and which may be acted on externally, so as to direct the blood components in the desired manner. The tubing connects the needle, the rotor, and the first and second containers. With the valving, the tubing is able to permit (i) the flow of whole blood from the needle to the rotor, (ii) the flow of anticoagulant from the first container to the whole blood flowing from the needle to the rotor, (iii) the flow of plasma from the rotor to the first container, and (iv) the flow of red blood cells from the rotor to the second container. The spinning means and the valving are preferably controlled by an electronic controller. Preferably, the system also includes pumping means, which is also controlled by the controller, and which forces the blood components out of the rotor to the tubing. The pumping means preferably includes means for drawing the whole blood into the rotor.

The system preferably includes an interlock device, connected to the controller, which does not permit the pumping (or flowing) of any blood components from the rotor until the needle has been inserted into the interlock device. This feature ensures that the donor is not still connected to the system when the system is generating pressure for forcing blood components out of the rotor. Preferably, the controller does not permit the rotor to be spun until the needle has been inserted into the interlock device.

In a preferred embodiment, the tubing has a valve, which is connected to three components: to the rotor by a common tube, to the second container by a second-container tube, and to the first container by a first-container tube. The tubing connecting the first container to the rotor is preferably in fluid communication with the needle, so that whole blood can preferably flow through the first-container tube through the valve to the rotor. In this embodiment, the controller includes means for detecting the presence of red blood cells passing from the rotor to the valve means, and causes the valve means to direct the red blood cells to the second container upon the detection of the red blood cells. In one embodiment, the needle is attached to the first-container tube.

In an alternative, preferred embodiment, the needle is connected to the valve means by a separate tube, so that the valve means is connected to four components: the rotor, the first and second containers, and the needle. In this embodiment, the valve means, in one mode, permits flow from the needle to the rotor while allowing anticoagulant to enter this flow at the valve means. In a second mode, the valve means permits no flow from the rotor. In a third mode, the valve means permits flow from the rotor to the first container, and in a fourth mode, the valve means permits flow from the rotor to the second container.

The variable-volume rotor is preferably of the type described in co-pending application Ser. No. 08/322,601 for a "Blood Processing System" by Headley and Powers, filed Oct. 13, 1994. This application is incorporated herein by reference. In a preferred embodiment of the invention, the rotor includes an elastic diaphragm and a rigid member, which together define a chamber of varying volume (as described in application Ser. No. 08/322,601). The pumping means in this embodiment may apply gas pressure against this diaphragm to force blood components out of the rotor, preferably through the common tube through the valve to their respective containers. The pumping means also preferably includes means for applying a negative gas pressure against the rotor's diaphragm in order to draw whole blood into the rotor's chamber.

In a preferred procedure, the system is connected to the donor for collecting the whole blood from the donor, then the system is disconnected from the donor and used to separate the blood into its components by centrifugation. Preferably, the system first draws whole blood through the needle and meters anticoagulant from the first container into the whole blood as it enters the variable-volume rotor. The anticoagulated whole blood then enters the rotor. When the system detects that the desired quantity of whole blood has entered the rotor, the needle is withdrawn from the donor's arm, following which the rotor is spun so as to separate the whole blood into plasma and red blood cells. After the blood components are separated, the rotor continues to spin to maintain the blood components in their separated state (preferably at a slower rate than that required to achieve the separation), and the plasma is forced out of the rotor and directed to the first container, which held the anticoagulant. Preferably, as noted above, the system is designed so that this forcing the plasma out of the rotor cannot take place until the needle is removed from the donor and inserted into an interlock device After all the plasma has been forced out of the rotor, the red blood cells are forced out and directed to the second container.

In an alternative embodiment of the process, the red blood cells are washed before being dispensed from the rotor. Wash solution is added to the rotor after the plasma has been directed from the rotor but before the red blood cells have been directed from the rotor. The rotor is then agitated so as to mix the wash solution and the red blood cells. After the wash solution and the red blood cells have been mixed, the rotor is spun again so as to separate the wash solution and the red blood cells. The separated wash solution is dispensed from the rotor, and then finally the washed, separated red blood cells are dispensed from the rotor.

DESCRIPTION OF SPECIFIC EMBODIMENTS

Figure 1:
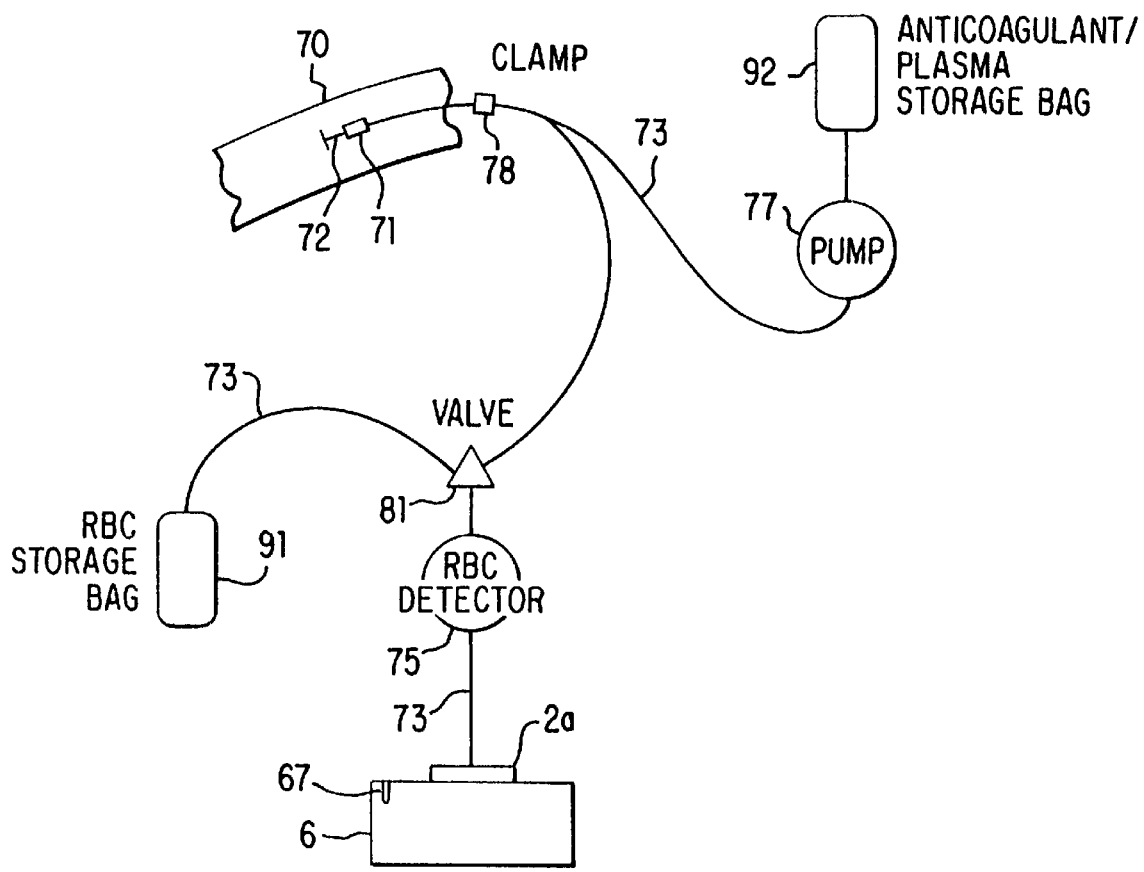
FIG. 1 is a schematic of a system according to a one embodiment of the present invention.
Figure 3:
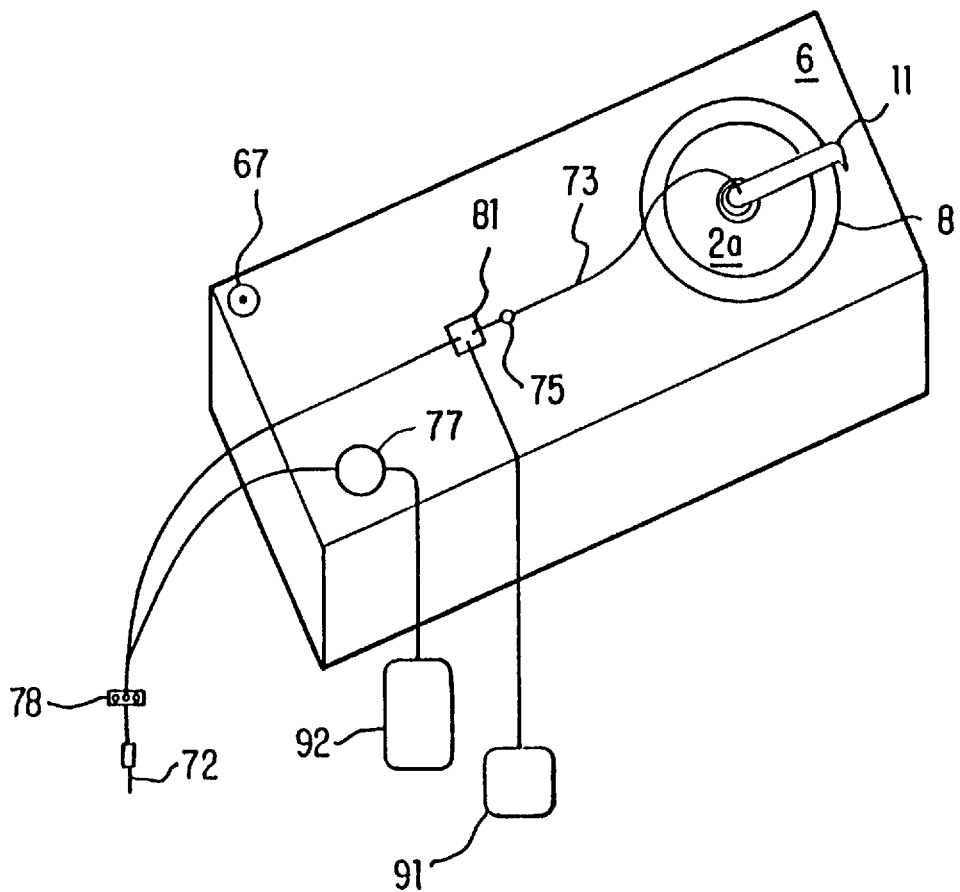
FIG. 3 is a perspective view of FIG. 1 system.
Figure 4:
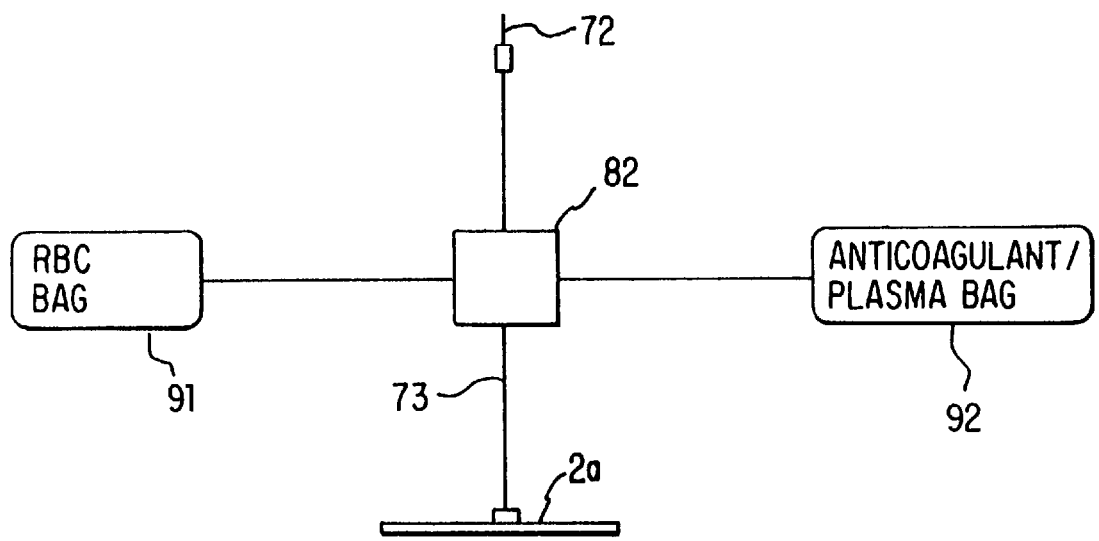
FIG. 4 shows the components of a disposable set for a preferred embodiment of the invention.

The separator of this invention disclosure, shown schematically in FIG. 1, consists of a sterile, closed-system disposable set in which the blood is collected and processed and a control unit 6 that interfaces with the disposable set and that controls the collection and separation process. One embodiment of the disposable set consists of a needle 72 through which blood is drawn from the donor 70 and a bag 92 containing an anticoagulant such as ACD, CPD or trisodium citrate. This bag 92 serves as the storage container for the plasma or platelet-rich plasma following the processing of the blood by the system. The disposable set also includes a second bag 91, which may contain a red cell preservative solution, and into which the red cells are directed for storage following separation. The set further includes a variable-volume rotor 2a, preferably of the type shown in FIGS. 1–4 of the above-referenced co-pending application Ser. No. 08/322,601, although other rotors shown and described in this co-pending application may be used as well, such as the rotors shown in FIG. 7, or FIG. 8A, or in FIGS. 20–22. These principal components of the system are joined by four lengths of tubing 73, two lengths of which are connected by the fitting 71 to which the needle 72 is attached, and three lengths of which are connected by a valve 81. Although, many different types of valves may be used in the present invention, one preferred embodiment of the invention uses a stopcock-type valve to direct the fluid in the desired manner. An alternative disposable set is shown in FIG. 4. In this embodiment, each of four lengths of tubing connect a valve means 82 to one of the other components of the disposable set, namely, the needle 72, the rotor 2a and the first and second containers 91, 92.

Figure 2:
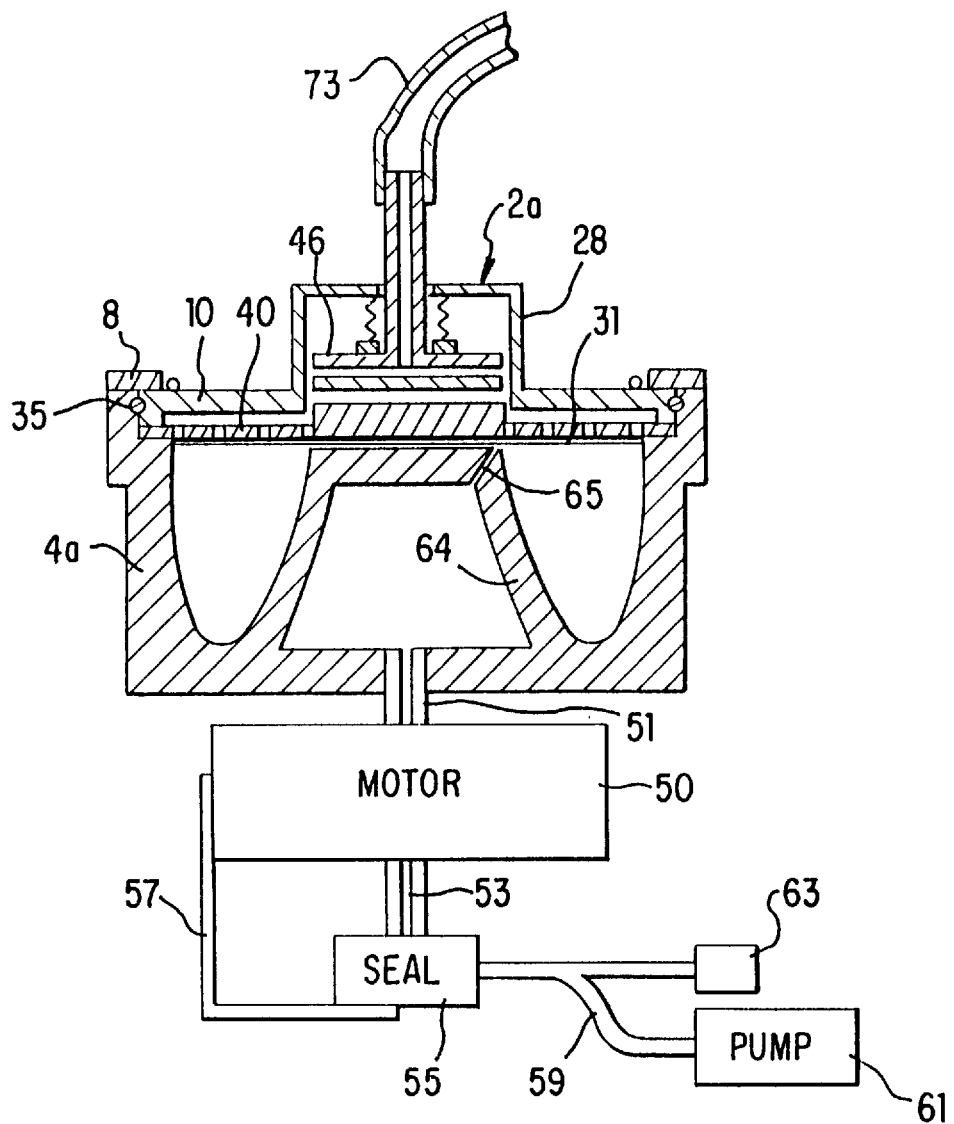
FIG. 2 shows a cross-section of a rotor and a chuck for holding and spinning the rotor that may be used in the present invention.

The non-disposable portion of the system includes mechanisms for spinning the rotor 2a and applying pressure to the rotor 2a to force fluid out of the rotor 2a. FIG. 2 shows the components of a preferred arrangement for spinning and pumping. A centrifuge chuck 4a holds the rotor 2a; the chuck 4a has a clamp 8 that holds the rotor 2a securely in place in the chuck, and an O-ring 35 that forms an air-tight seal. A drive motor 50 is connected to the chuck 4a by means of a shaft 51. In order to apply pressure to the rotor 2a to pump fluid out of the rotor, the shaft 51 has an axial hole through its center 53 and is connected to a rotary pneumatic seal 55, which in turn is connected by tubing 59 to a compressor/vacuum pump 61 and to a controllable exhaust valve 63. Holes 65 in the interior of the chuck 4a allow air to flow to and from the compressor/vacuum pump 61.

These spinning and pumping mechanisms are preferably disposed in a control unit 6. The control unit, as shown in FIG. 3, may also incorporate a device, such as a pump 77, suitable for metering the anticoagulant from the anticoagulant bag 91 into the whole blood in the proper ratio at the distal end of the needle 72 as the blood is being drawn from the donor. The anticoagulant metering mechanism 77 is also shown schematically in FIG. 1.

To use the system, the rotor 2a is clamped in the centrifuge chuck 4a, as shown in FIG. 2, and the tubing that connects the anticoagulant bag 92 to the needle 72 is placed in the anticoagulant mechanism 77, which may be a pump or other metering device, as shown in FIG. 3. The needle 72 is inserted into a vein in the donor's arm, as shown in FIG. 1, and the anticoagulant metering mechanism 77 is activated. Since the anticoagulant is metered into the whole blood as it is drawn, anticoagulant shock to the red cells is minimized. The anticoagulated blood flows from the donor, through the tubing and into the rotor 2a by a combination of gravity and venous pressure and, if needed, by vacuum from the compressor/vacuum pump 61. The pump 61 may be designed with a safe maximum drawing vacuum to avoid exposing the donor to high drawing vacuums. The amount of blood collected may be determined by weighing the rotor 2a, or, alternatively, whole blood may be allowed to flow into the rotor 2a until the rotor is full, at which point the collection can be stopped.

It should be noted that, while a standard unit of whole blood is defined by regulations in the United States and in other countries as equal to 450 ml+/−45 ml, the definition of a unit of whole blood may be defined differently in some other countries. In the present invention, the system may be designed and manufactured to comply with whatever definition is appropriate.

When the desired amount of whole blood (usually one unit) has been collected, a tubing clamp 78 (shown in FIG. 3 and schematically in FIG. 1) occludes the tubing leading to the needle 72. The needle 72 is then withdrawn from the donor's arm 70, and the needle 72 is then inserted into an interlock slot 67 in the control unit 6. This interlock slot 67 assures that component processing cannot begin until the needle 72 has been removed from the donor's arm 70 and thereby eliminates the need for donor-protection safety devices such as air sensors and pressure detectors. (This interlock slot may also include a sharps-disposal feature, which removes the needle 72 from the disposable set in a safe manner so that there is no risk to personnel of contamination.)

At this point, the rotor 2a contains approximately one unit of anticoagulated whole blood and the elastic wall 31 of the rotor is fully distended so that it is in contact with the interior surface of the chuck 4a and conforms to the shape of the chuck. The motor 50 is then activated, and the separation of the blood components begins, proceeding in a manner similar to that described in the above-referenced application Ser. No. 08/322,601. As the rotational speed of the chuck 4a increases, the red cells, which are the heaviest component, are forced to the outer periphery of the rotor 2a, while the platelets and plasma, which are lighter, are nearer the center of rotation. The blood is subjected to centrifugal force for only as long as is necessary to separate the red cells from the platelet-rich plasma.

When the separation is complete, the compressor 61 begins to pump compressed air into the chuck 4a. When the air pressure outside the elastic wall member 31 exceeds the fluid head from the radius of the elastic wall member 31 to the skirt of the collector 46, the platelet-rich plasma begins to flow out of the rotor 2a and into the bag 92 from which the anticoagulant had been metered into the whole blood. The rotational speed of the chuck 4a may be reduced at this point in the process to a level that is just high enough to maintain component separation. Reducing the rotational speed has the effect of reducing the amount of air pressure necessary to overcome the fluid head described above.

The air pressure causes the elastic wall member 31 of the rotor 2a to change its shape to accommodate the gradual reduction of the volume of fluid in the rotor 2a. When all of the platelet-rich plasma has been forced out of the rotor 2a, an electro-optical device 75 on the outlet line from the rotor detects the presence of red cells in the tubing and causes valve 81 to close the line leading to the plasma bag 92 and open the line leading to the red cell storage bag 91, which may contain storage solution for the long-term storage of red blood cells. (A portion of the valve 81 may be made part of the disposable portion of the system and be acted upon by the control unit 6 to direct flow towards either bag 91, 92.) At this point, the rotor 2a can be brought to a full stop. The compressor 61 continues pumping compressed air into the space between the chuck 4a and the elastic wall member 31 until all of the red cells have been forced out of the rotor 2a and into the red cell storage bag 91. At this point, the machine stops. The attendant then seals the lines leading to the two storage bags 91, 92 and disconnects them from the rotor 2a. All of the parts of the processing set, other than the two storage bags 91, 92, are then disposed of.

Figure 5:
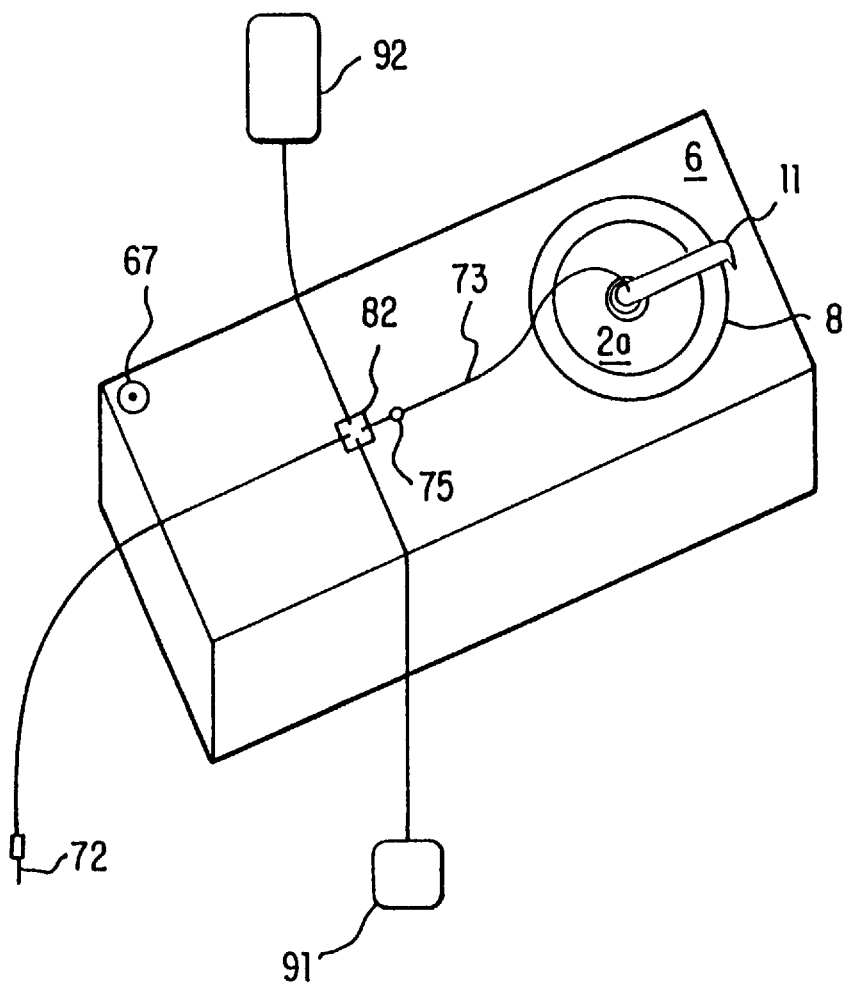
FIG. 5 is a perspective view of a system using the FIG. 4 disposable set.

The embodiment shown in FIG. 5, which uses the disposable set of FIG. 4, works in a similar manner. The valve means 82 in the FIG. 4 disposable set has four modes: in the first mode, it permits the flow of whole blood from the needle 72 to the rotor 2a while metering anticoagulant from the first container 92 into the whole blood; in the second mode, it permits no flow out of the rotor 2a; in its third mode, the valve means 82 permits flow of plasma from the rotor 2a to the first container 92; and in its fourth mode, it permits flow of red cells from the rotor 2a to the second container 91. When the rotor 2a is full, the control unit 6 urges the valve means 82 into its second mode to prevent flow out of the rotor 2a or to the needle 72. The needle 72 is then withdrawn from the donor's arm 70, and inserted into an interlock slot 67 in the control unit 6. The insertion of the needle 72 into the interlock slot 67 allows the component processing to continue. The motor 50 is then activated, and the separation of the blood components begins.

When the separation is complete, the valve means 82, moves to its third mode, wherein it permits flow from the rotor 2a to the first container 92. The compressor 61 begins to pump compressed air into the chuck 4a, in order to force the separated plasma to the first container 92. As in the FIG. 3 embodiment, the rotational speed of the chuck 4a may be reduced at this point in the process to a level that is just high enough to maintain component separation. When all of the platelet-rich plasma has been forced out of the rotor 2a, an electro-optical device 75 on the outlet line from the rotor detects the presence of red cells and causes valve 82 to enter the fourth mode, thereby closing the line leading to the plasma bag 92 and opening the line leading to the red cell storage bag 91, which preferably contains a red-cell preservative solution. Either or both of the lines leading to the containers may include filters, in order to filter the plasma or red blood cells as they are sent to the container. At this point, the rotor 2a can be brought to a full stop. The compressor 61 continues pumping compressed air into the space between the chuck 4a and the elastic wall member 31 until all of the red cells have been forced out of the rotor 2a and into the red cell storage bag 91. The machine then stops, and the lines leading to the two storage bags 91, 92 are sealed and disconnected from the rotor 2a.

Recently published statistics indicate that platelet needs of patients are increasingly being met with single-donor platelets collected by apheresis rather than with pooled, random donor platelets separated from whole blood. As a consequence, the trend in blood banking is to process whole blood into just two components, namely, packed red blood cells (RBCs) and plasma. The system described above can also be used to separate platelets and to prepare platelet-poor plasma.

For example, the system can be used to collect packed RBCs and platelet-poor plasma (PPP) by running the centrifuge either longer or at a higher speed or both prior to pumping in compressed air to displace the plasma. The additional centrifugal force causes the platelets to sediment out of the plasma, so pure plasma is collected in the plasma bag.

If the blood bank desires to collect platelets, RBC and plasma all in separate bags, a third bag is needed in the disposable set. In this version of the system, the blood is centrifuged hard enough to have the platelets form a layer on the RBC. The compressed air displaces first the plasma and then the platelets prior to displacing the RBC. When the electro-optical device senses the presence of the platelets, the device closes the valve to the plasma bag and opens the valve to the platelet bag. Then, when the electro-optical device senses RBCs, the device closes the valve to the platelet bag and opens the valve to the RBC bag.

The system described herein can also be used to separate the buffy coat, which contains white blood cells (WBCs), platelets, and some red cells. To collect the buffy coat, the system senses when the platelets are exiting from the spinning rotor. The effluent from the rotor is then directed into a separate bag until such time as the system detects that only red cells are exiting from the rotor. After the red cells have been removed from the rotor, the buffy coat can be further processed, if desired, to separate the platelets for transfusion.

In any centrifugation process, it is inevitable that some WBCs remain with the RBCs. There is increasing evidence that it is desirable to remove as many of the WBCs from the RBCs as possible prior to transfusion of the RBCs. Depletion of the WBC content of the RBCs can be accomplished by means of the buffy coat method described above. Alternatively, the disposable set can incorporate an integral WBC filter through which the RBCs are passed before being directed to the RBC storage bag 91.

Alternate versions to the systems described above would have the centrifuge spinning during the collection phase so that the blood would be essentially already separated when the needle is removed from the donor. The interlock 67 still prevents compressed air from being pumped into the rotor to express the components into their respective bags while the needle 72 is still in the donor's arm.

Research has shown that washing red cells after separation from whole blood may result in lower white cell contamination and also may permit the red cells to be stored in the liquid state (i.e., not frozen) for up to 10 weeks. If it were desired to wash the red cells after separation, this could be accomplished with the separator by the use of an alternative disposable set that includes a bag of wash solution, such as saline, and a waste bag—or the wash-solution bag may double as the waste bag. The component separation would proceed as described above, but when the electro-optical device detects RBCs emerging from the rotor, instead of diverting them to the RBC bag as above, it would initiate the wash cycle.

In the wash cycle, the chuck is vented to atmosphere and brought to a stop. The valve to the wash-solution bag would be opened, allowing wash solution to enter the rotor, and the rotor would be agitated slowly back and forth. When the rotor was full and the RBCs thoroughly mixed with the wash solution, the centrifuge would restart. After sufficient time for the RBCs to be fully separated from the wash solution, the valve to the waste bag (which may be the wash-solution bag) would be opened and, as in the above systems, compressed air would be pumped into the rotor, forcing the wash solution out into the waste bag. When the electro-optical device detected RBCs emerging from the rotor, the valve to the waste bag would be closed and the RBCs diverted to their own collection bag. Other wash techniques may also be used.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A method of collecting into a collection system a volume of whole blood from a donor, the method comprising the steps of:
   connecting the donor to the collection system;
   disconnecting the donor from the collection system; and
   using the collection system to separate the blood into its components by centrifugation,
   wherein the blood is collected and processed in a variable-volume rotor, further including the step of
      providing an interlock device to prevent the collection system from pumping processed blood components from the rotor until the donor has been disconnected from the collection system, and a controller for controlling flow to and from the rotor, wherein the controller does not permit pumping from the rotor until a portion of the collection system is inserted into the interlock device indicating that the donor has been disconnected from the collection system.

2. A method according to claim 1, wherein the collection system is provided with first and second containers, and further including the step of
   after the blood is separated into first and second components, directing the first component from the rotor to the first container and directing the second component from the rotor to the second container.

3. A method according to claim 2, wherein the first component includes plasma and the second component includes red blood cells, and further including the steps of
   providing anticoagulant in the first container; and
   introducing anticoagulant from the first container to the blood, as the blood is drawn from the donor into the collection system.

4. A method according to claim 3, further including the step of providing red-blood-cell storage solution in the second container.

5. A method of collecting into a collection system a volume of whole blood from a donor, the method comprising the steps of:
   connecting the donor to a collection system having a rotor;
   disconnecting the donor from the collection system; and
   using the collection system to separate the blood into its components by centrifugation,
   wherein the blood is collected and processed in the rotor, further including the step of
      providing an interlock device to prevent the collection system from pumping processed blood components from the rotor until the donor has been disconnected from the collection system, and a controller for controlling flow to and from the rotor, wherein the controller does not permit pumping from the rotor until a portion of the collection system is inserted into the interlock device indicating that the donor has been disconnected from the collection system.

6. A method according to claim 5, wherein the collection system is provided with first and second containers, and further including the step of
   after the blood is separated into first and second components, directing the first component from the rotor to the first container and directing the second component from the rotor to the second container.

7. A method according to claim 6, wherein the first component includes plasma and the second component includes red blood cells, and further including the steps of
   providing anticoagulant in the first container; and
   introducing anticoagulant from the first container to the blood, as the blood is drawn from the donor into the collection system.

8. A method according to claim 7, further including the step of providing red-blood-cell storage solution in the second container.

9. A method of collecting into a collection system a volume of whole blood from a donor, the method comprising the steps of:
   providing a collection system having a centrifuge rotor for receiving the blood;
   connecting the donor to the collection system;
   drawing blood from the connected donor into the collection system without returning blood components to the donor;
   disconnecting the donor from the collection system after the blood is drawn from the donor;
   using the collection system to separate the blood into first and second components by centrifugation; and
   removing the first component from the rotor into a storage container,
   wherein the collection system is provided with a second storage container, and further including the step of directing the second component from the rotor to the second container; and
   wherein the first component includes plasma and the second component includes red blood cells, and further including the steps of
      providing anticoagulant in the first storage container; and
      introducing anticoagulant from the first storage container to the blood, as the blood is drawn from the donor into the collection system.

10. A method according to claim 9, further including the step of providing red-blood-cell storage solution in the second storage container.

11. A method of collecting into a collection system a volume of whole blood from a donor, the method comprising the steps of:
    providing a collection system having a centrifuge rotor for receiving the blood;
    connecting the donor to the collection system;
    drawing blood from the connected donor into the collection system without returning blood components to the donor;
    disconnecting the donor from the collection system after the blood is drawn from the donor;
    using the collection system to separate the blood into first and second components by centrifugation; and
    removing the first component from the rotor into a storage container,
    wherein the blood is collected and processed in a variable-volume rotor, wherein the collection system is provided with first and second containers, and further including the step of
    after the blood is separated into first and second components, directing the first component from the rotor to the first container and directing the second component from the rotor to the second container, and wherein the first component includes plasma and the second component includes red blood cells, and further including the steps of
       providing anticoagulant in the first container; and introducing anticoagulant from the first container to the blood, as the blood is drawn from the donor into the collection system.

12. A method according to claim 11, further including the step of providing red-blood-cell storage solution in the second container.

13. A method of collecting into a collection system a volume of blood from a donor, the method comprising the steps of:

connecting the donor to a collection system having a centrifuge rotor and a first container, wherein the first container includes anticoagulant;

drawing blood from the connected donor into the collection system;

introducing anticoagulant from the first container to the blood, as the blood is drawn from the donor into the collection system;

disconnecting the donor from the collection system, after blood is drawn from the donor to the collection system;

using the collection system to separate the blood into plasma and red blood cells by centrifugation, wherein the blood is collected and processed in the rotor; and directing, after the blood is separated into plasma and red blood cells, the plasma from the rotor to the first container.

14. A method according to claim 13, wherein the collection system includes a second container, and the method further includes the steps of providing red-blood-cell storage solution in the second container; and directing, after the blood is separated into plasma and red blood cells, the red blood cells from the rotor to the second container.

15. A method of collecting into a collection system a volume of blood from a donor so as separate the blood into components, the method comprising the steps of:

providing a collection system having a centrifuge rotor for receiving the blood;

connecting the donor to the collection system;

drawing the blood from the connected donor into the collection system;

disconnecting the donor from the collection system after the blood is drawn from the donor;

using the collection system to separate the blood into first and second components by centrifugation; and removing the first component from the rotor into a first storage container after the collection system is disconnected from the donor, further including the step of removing the second component from the rotor into a second storage container, wherein the first component includes plasma and the second component includes red blood cells, and further including the steps of providing anticoagulant in the first storage container; and introducing anticoagulant from the first container to the blood, as the blood is drawn from the donor into the collection system.

16. A method according to claim 15, further including the step of providing red-blood-cell storage solution in the second container.

* * * * *